United States Patent [19]

Shan

[11] Patent Number: 5,728,044

[45] Date of Patent: Mar. 17, 1998

[54] SENSOR DEVICE FOR SPACIAL IMAGING OF ENDOSCOPES

[76] Inventor: Yansong Shan, 42149 Hartford Dr., Canton, Mich. 48187

[21] Appl. No.: 401,855

[22] Filed: Mar. 10, 1995

[51] Int. Cl.$^6$ .................................................. A61B 1/012
[52] U.S. Cl. .............................. 600/145; 600/117; 33/512
[58] Field of Search ............................ 600/103, 104, 600/117, 145; 33/533, 544, 555, DIG. 13, 511, 512, 514.2, 542; 73/865.8

[56] References Cited

U.S. PATENT DOCUMENTS

| | | | |
|---|---|---|---|
| 4,233,748 | 11/1980 | Ford et al. | 33/286 |
| 4,570,354 | 2/1986 | Hindes | 33/542 |
| 4,651,436 | 3/1987 | Gaal | 33/533 |
| 4,873,965 | 10/1989 | Danielli | 128/6 |
| 4,910,877 | 3/1990 | Sokol | 33/544 |
| 5,060,632 | 10/1991 | Hibino | 128/6 |

FOREIGN PATENT DOCUMENTS 4146716  5/1992  Japan ................... 600/101

OTHER PUBLICATIONS

Bladen, J.S., et al., "Non-Radiological Technique for Three Dimensional Imaging of Endoscopes,"*The Lancet*, pp. 719–722, vol. 341, Mar. 20, 1993.

*Primary Examiner*—Richard J. Apley
*Assistant Examiner*—John P. Leubecker
*Attorney, Agent, or Firm*—James M. Deimen

[57] ABSTRACT

A sensor device and system projects a three-dimensional image of the position of the colonoscope within the gut onto a video screen next to the optical image from the end of the colonoscope. The sensor device comprises a plurality of strain gages mounted on a bendable rod at the head of the rod. As the head is pushed through the biopsy channel of the colonoscope, the head bends with the curvature of the colonoscope causing the deformation of the head to be captured by the strain gages. An encoder at the inlet to the biopsy channel records the velocity and distance of the head as the head is pushed in and through the channel. The combined electrical output from the strain gages and encoder enables an instantaneous generation of a three-dimensional image of the colonoscope on a view screen. The sensor device avoids the need for any equipment that is above or surrounds the abdomen of the patient.

13 Claims, 4 Drawing Sheets

SENSOR DEVICE FOR SPACIAL IMAGING OF ENDOSCOPES

BACKGROUND OF THE INVENTION

The field of the invention pertains to endoscopes and, in particular, to the position of an endoscope as it is advanced through an orifice in the human body. The position is of particular importance in advancing a colonoscope through the gut because of the convoluted shape of the gut and the danger of damage to the gut wall at locations of steep curvature and loop.

A variety of techniques have been used to visualize the colonoscope as it is advanced in the gut. Perhaps the most obvious technique is fluoroscopy. Unfortunately, fluoroscopy requires expensive, bulky and awkward equipment externally positioned over the patient. Fluoroscope time is generally a scarce resource in even the best equipped medical centers. Most important is the extended time period of x-radiation exposure to the patient, endoscopist and other hospital personnel.

To avoid the use of fluoroscopy other approaches to measuring the position and, in particular, the curvature of the colonoscope as it is advanced through the colon have been proposed. Magnetic field sensors have had some experimental development. In one approach, miniature inductive sensors were placed within the biopsy channel of an endoscope. A magnetic field was created around the exterior of the patient. As the sensors were moved through the biopsy channel an electric signal was generated and the signals monitored by a computer which calculated the path of the sensors as they moved through the biopsy channel. Since the biopsy channel follows through the endoscope, the position and configuration of the endoscope can be generated by the computer to provide a three dimensional image of the endoscope. This magnetic field sensor is disclosed in Bladen, I. S. et al.: "Non-Radiological Technique For Three Dimensional Imaging Of Endoscope", The Lancet, pp. 719–722, Vol. 341: Mar. 20, 1993.

A similar study was done with a magnetic field and coil to generate an image of the endoscope in the colon during motion of a sensor rod. This study was reported in Williams, Christopher, et al.: "Electronic Three-Dimensional Imaging Of Intestinal Endoscope", The Lancet, pp. 724–725, Vol. 341: Mar. 20, 1993.

The magnetic approach has several disadvantages. The first system above requires several low frequency magnetic field generators in order to obtain the signals from the sensor. Thus, the system is expensive and cumbersome with portions that cover the patient's entire abdomen thus interfering with the endoscopic procedure. Moreover, a nonmetallic operating platform or bed is required and the patient must not move during the detection period. Similar problems arise with the second system above.

Devices to measure the curvature of pipes without external field devices, whether radiative or magnetic, have been developed for inspecting steam generators in nuclear power facilities. Disclosed in U.S. Pat. No. 4,651,436 is a bendable plug that is moved through a pipe. As the plug moves and bends, sensors communicate the changes in bending of the plug to electrical measurement means for the sensors. In particular, FIG. 5 shows strain gages on the exterior of a flexible tube.

U.S. Pat. No. 4,910,877 shows a similar flexible device adapted to pass through steam generator pipes and provide an electrical signal from a strain gage as the device negotiates bends in the pipes. These devices, however, are relatively large, on the order of inches in diameter, and need only negotiate a few degrees of bend.

More directly related to endoscopes and measurement of the position and posture of the device is U.S. Pat. No. 5,060,632 wherein FIG. 101 shows curvature sensors on the exterior of a bendable portion near the tip of the endoscope. The bent state is monitored electrically as the external controls on the endoscope are manipulated to bend the endoscope during advancement. Thus, the curving path of the head of the endoscope can be monitored as the head advances. Means to cause the head to bend are also shown in U.S. Pat. No. 4,873,965.

SUMMARY OF THE INVENTION

The principal object of the new sensor device is a simple, easy to use visualization system which projects a three dimensional image of the position of the colonoscope onto a video screen next to the optical image from the end of the colonoscope.

Further objects of the new sensors comprise a device that avoids use of an "external field" or any equipment that surrounds or is positioned about the patient. Only the colonoscope itself is positioned inside and adjacent the patient.

Moreover, the new sensor device may be employed with existing colonoscopes because the sensors are moved through the biopsy channel of the colonoscope. An important feature of the sensors is the option of advancing and retracting the sensors within the colonoscope as the colonoscope is periodically advanced or withdrawing and reinserting the sensors as necessary when the biopsy channel is to be used for other purposes.

The sensor device comprises a plurality of sensors in the form of tiny strain gages mounted on a bendable rod at the head of the rod. As the head is pushed through the biopsy channel of the colonoscope the head bends with the curvature of the colonoscope causing the deformation of the head to be captured by the strain gages. The instantaneous deformation of the strain gages can be captured electrically as the head is pushed through.

An encoder at the inlet to the biopsy channel records the velocity and distance of the head as the head is pushed in and through the channel. The combined electrical information from the strain gages and encoder enables an instantaneous generation of a three-dimensional image of the colonoscope. This image can be placed on a view screen convenient to the physician operating the colonoscope.

The cross-sectional area of the sensor rod can be reduced in size to allow insertion into the smallest biopsy channels including pediatric endoscopes. Thus, this sensor device can be used for all types of endoscopy including small bowel enteroscopy wherein the tortuosity of the small bowel causes particular difficulty.

DESCRIPTION OF THE PREFERRED EMBODIMENT

Figure 1:
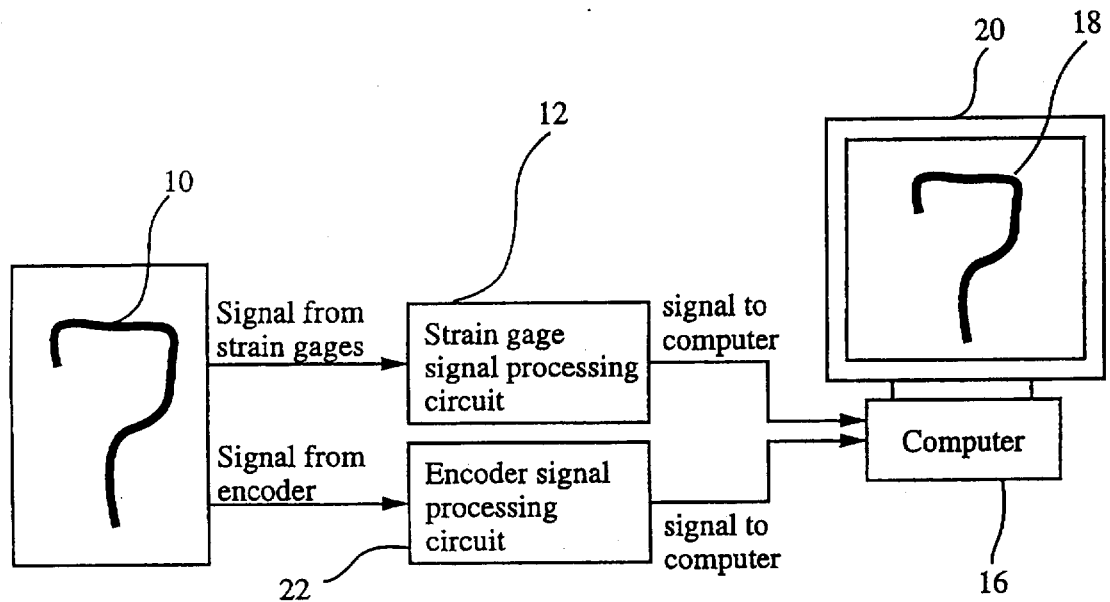
FIG. 1 illustrates the overall structure of the imaging system for the sensor device.

FIG. 1 depicts the sensor device or rod 10 and colonoscope inside a patient during use. The electric signals from the strain gages of the sensor device 10 are communicated to a strain gage signal processing circuit 12 and then fed to a computer 16 for calculation and display of an image 18 on a view screen 20.

A second set of electric signals from the optical encoder representing the velocity and distance of the head of the sensor device as it is advanced in the biopsy channel of the colonoscope is communicated to an encoder signal processing circuit 22. The encoder electric signals are then fed to the computer 16 for the calculation and display of the image 18.

Within the strain gage signal processing circuit 12 are a plurality of Wheatstone bridge circuits, each circuit having as one element an individual strain gage of the sensor device 10. Where a large number of individual strain gages are employed the strain gage signal processing circuit 12 may employ an analog multiplexer circuit controlled by the computer 16 to selectively and sequentially query the strain gages.

Figure 2:
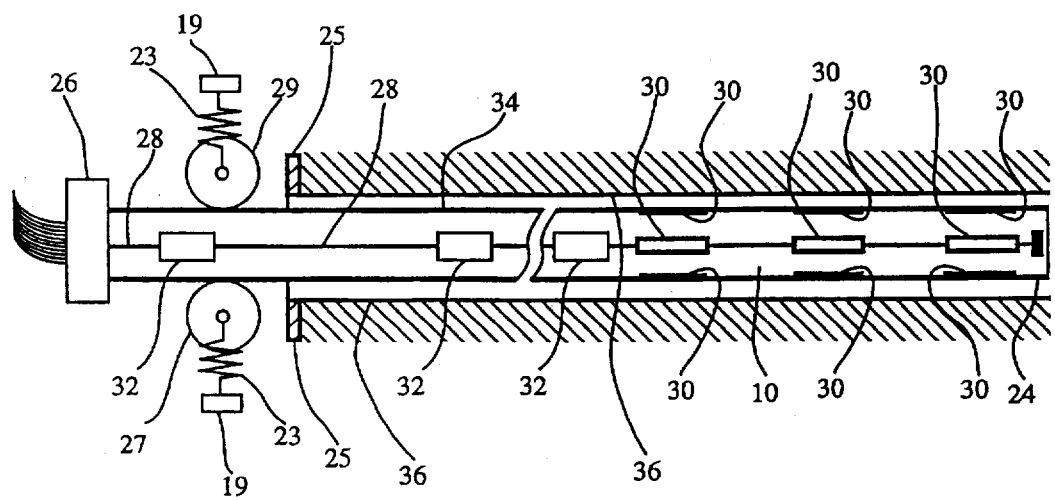
FIG. 2 illustrates the basic structure of the sensor rod.

FIG. 2 depicts schematically the sensor device or rod 10 from head 24 to electrical connector 26. The sensor rod 10 is constructed of silicone rubber having a stainless steel wire 28 down the center axis of the rod. The wire 28 reinforces the rod and substantially prevents the elongation of the rod 10. The wire 28 and silicone rubber is sufficiently flexible to conform the rod 10 to the shape of the biopsy channel but return the rod to a straight shape when retracted from the biopsy channel.

Figure 3:
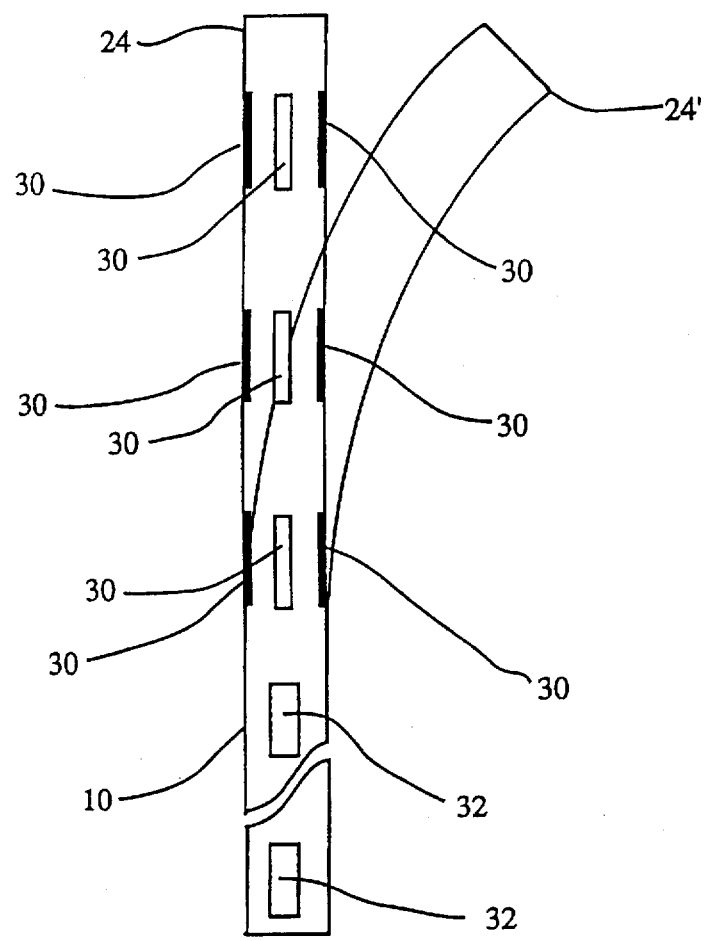
FIG. 3 illustrates the strain gage configuration on the head of the sensor rod.

A plurality of strain gages 30, 32 are affixed to the exterior of the rod 10 with wires leading to the electrical connector 26. The electrical connector 26 interfaces with the signal processing board of the signal processing circuit 12. The strain gages 30 at the head 24 of the rod 10 are positioned to measure bending as best shown in FIG. 3 wherein the gages are positioned at 90° intervals about the rod in one or more axial locations. The portion of the rod 10 having the bending strain gages 30 comprises the head 24. The base of the head 24 is a location spaced just beyond the band of bending strain gages 30 most remote from the tip of the head. Torsional strain gages 32 are spaced along the length of the rod 10.

The entire rod 10 is encased in a polytetrafluoroethylene coating 34 to protect the strain gages 30, 32 from abrasion and liquids present in the environment. The coating also permits the rod 10 to be easily advanced and retracted through the biopsy channel. The coating may be coated onto the rod in any conventional manner, however, a shrink fit polytetrafluoroethylene tube has been found most advantageous and economical.

Adjacent the inlet 25 of the biopsy channel is the encoder wheels 27 and 29 on opposite sides of the sensor rod 10. The encoder wheels 27 and 29 are urged into firm contact with the sensor rod 10 by springs 23 fastened to a base 19. One of the wheels 27 serves as an idler and the other wheel 29 drives an optical rotary encoder to provide an electric signal in response to rotation of wheel 29. The rotation of wheel 29 is caused by linear movement of the sensor rod 10 into the biopsy channel 36. Thus, the encoder wheel 29 provides a measure of distance versus time for the movement of the head 24 through the biopsy channel 36.

As best shown in FIG. 3, the head 24 is about 100 mm in length as equipped with the bending strain gages 30. When the head is bent, as shown at 24', the gages to the inside of the curve are put in compression and the gages to the outside of the curve are put in tension.

The torsional strain gages 32, however, are located beginning on the head 24 and along the remaining portion of the rod 10 which may extend 1500–1800 mm to the electrical connector 26. As noted above, the entire rod 10 assembly is encased in the polytetrafluoroethylene coating or shrink fit tube.

Figure 4:
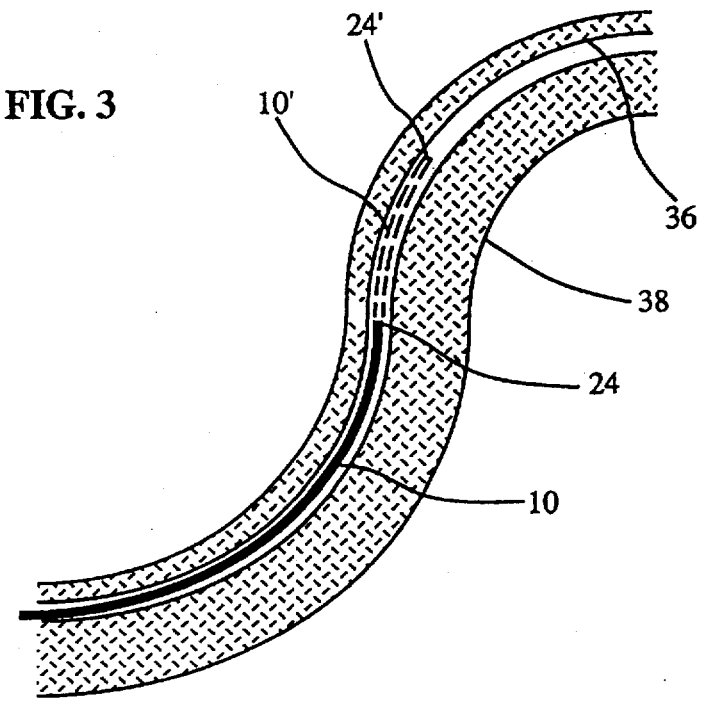
FIG. 4 illustrates the sensor head and rod navigating the biopsy channel in a colonoscope.

As shown in FIG. 4 the rod with the head 24 is advanced 10', 24' through the biopsy channel 36 of a colonoscope 38. In this mode of use, the colonoscope 38 is not advanced as the sensor rod 10 is advanced. Once the head 24 of the sensor rod 10 reaches the tip of the colonoscope a complete picture of the current location of the colonoscope will be obtained.

Figure 5:
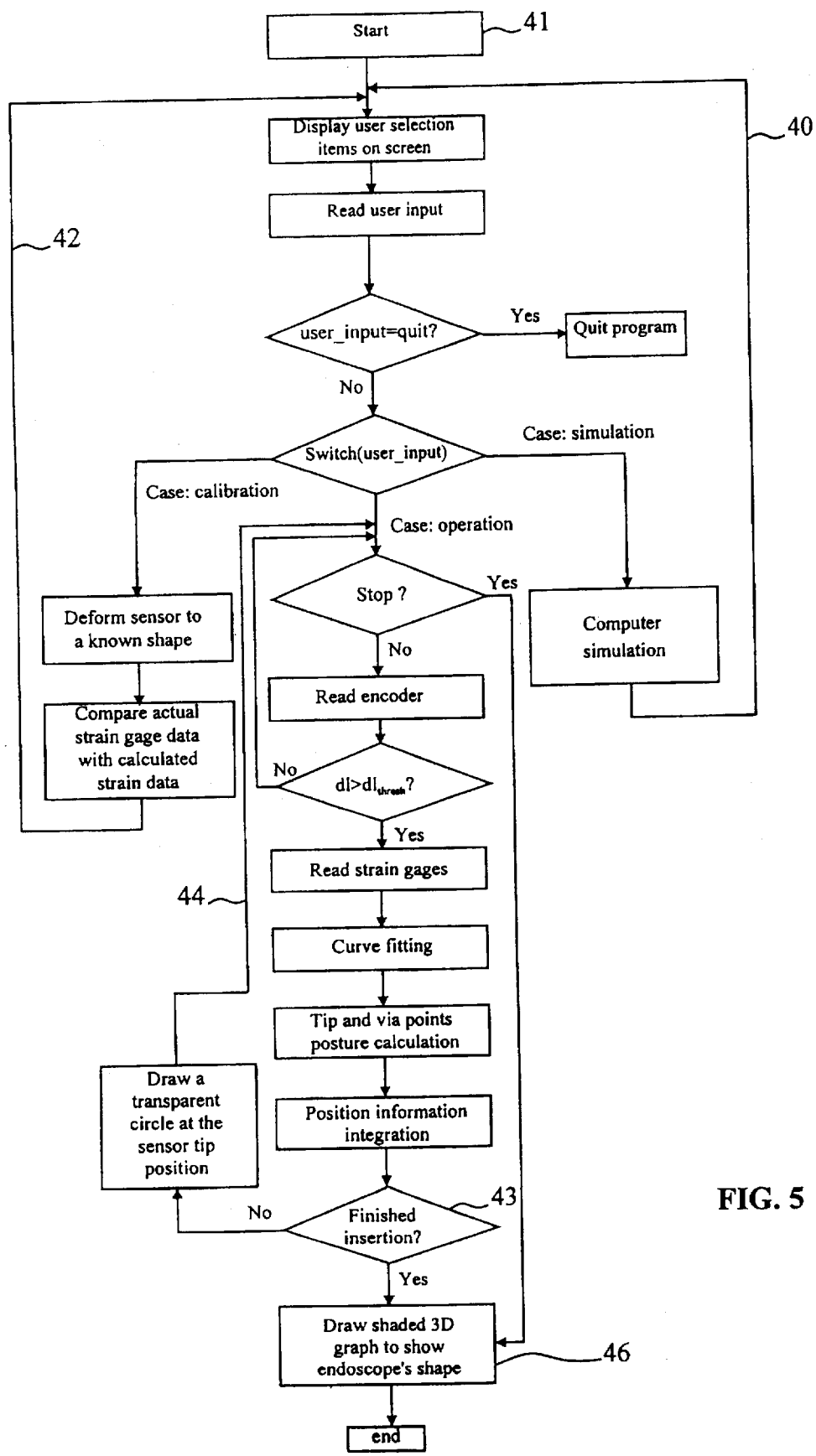
FIG. 5 is a flow diagram of the basic software for the imaging system.

FIG. 5 depicts the overall software flow diagram for the computer 16. The main program to calculate the path of the rod 10 and head 24 comprises the center vertical column of flow chart symbols beginning with "Start" 41 and ending with "Finished insertion?" 43. The computer 16 repeatedly reads the encoder wheel 29 position and strain gages 30 and 32 to calculate the position of the circular tip of the head 24. The calculated tip position of the head 24 is displayed as an ellipse to indicate the posture of the circular tip of the head 24. The displayed center of the ellipse indicates the position of the tip and the orientation of the ellipse indicates the orientation of the plane of the circular tip. The series of calculated and displayed centers of the ellipses are the via points which depict the path of the head 24 as a line of points determined by distance from the inlet 25 of the biopsy channel 36. These points form the path of the display 18 on the view screen 20.

The side loops of the flow diagram provide useful additional features. The loop to the right 40 provides for a simulation program as a training aid by simulating the encoder output and the strain gage 30, 32 outputs. Such a built in software simulator provides an excellent training tool without the need for any additional hardware.

The upper loop to the left 42 is a calibration sequence for the sensor rod 10 and head 24. Since the rubber sensor rod 10 and head 24 are typically more flexible than the strain gage 30, 32 elements fastened to the rod 10 and head 24, the strain gages tend to slightly distort the rubber in resisting the bending. As a result, these strain gages tend to reflect less bending than is actually occurring.

To calibrate, the sensor rod 10 and head 24 are deformed to a specified curved shape and the actual output of the strain gages 30, 32 compared with calculated strain data for the curved shape. Each sensor rod 10 and head 24 can be calibrated just before use thus assuring a more accurate depiction of the sensor device 10 on the view screen 20.

The lower loop to the left 44 draws the tip circles as a series of points about the tip point with each tip point iteration, the circles actually appearing as the ellipses on the view screen. When the final tip point is reached at the end of the biopsy channel, an optional program at 46 connects the ellipses and shades the space therebetween to provide a more realistic look to the image 18 of the colonoscope on the view screen 20.

Since a view screen 20 is two dimensional and the desire is to present three dimensional information to the viewer, the overall size of each ellipse depicts the distance from the viewer, more particularly, the depth of the sensor rod 10 and head 24 below the wall of the abdomen of the patient. Thus, smaller ellipses represent greater depth within the abdomen. The user can thereby visually instantly judge depth within the abdomen.

Figure 6:
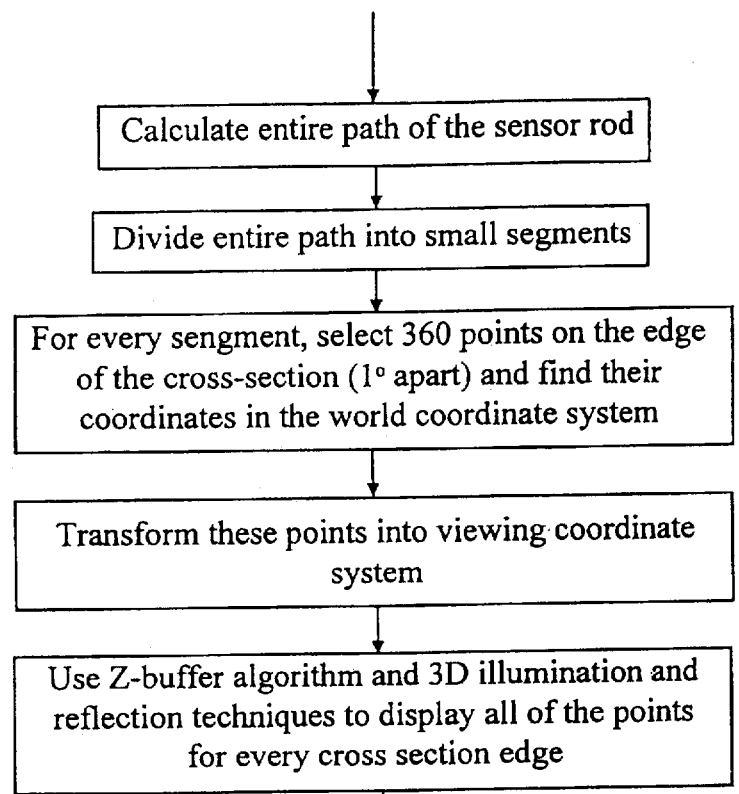
FIG. 6 is a flow diagram for the software that provides for three dimensional information on the view screen of the imaging system.

FIG. 6 depicts the flow diagram for the optional creation of a more realistic three dimensional image of the colonoscope. When the sensor rod 10 reaches the end of the biopsy channel 36, the entire path through the via points is calculated. Then the path between each two ellipses is divided into twenty equal segments and an ellipse calculated for each segment. Using a Z-buffer algorithm to delete portions of ellipses behind other points and a three dimensional illumination and reflection technique to shade the image, a realistic appearing three-dimension image of the colonoscope is displayed.

The calculation of the via and tip points is based on a kinematic model using the world coordinate system located at inlet 25 of the biopsy channel and the moving coordinate system on the head 24 at the base of the head. The position of the tip of the head 24 can then be calculated from the outputs of the bending strain gages 30 on the head relative to the moving coordinate system at the base of the head. The position and posture of the moving coordinate system is calculated and recorded. At any time, the moving coordinate system is in the position that was occupied by the head in the previous time interval. The distance of the base coordinate to its position in the previous time interval is the insertion length which is measured by the encoder. Therefore, based on the head position information from the previous time interval which is calculated based on the bending strain gages, the relationship between the moving coordinate system and the moving coordinate system in the previous time interval can be calculated. In turn, through the relationship of the world coordinate system and the moving coordinate system the position of the tip on the sensor head 24 can be ascertained within the patient's body. The calculation of the tip position is reiterated for intervals of time as the sensor rod 10 is pushed through the biopsy channel 36 until the end of the channel is reached. Since distance of the sensor rod 10 in the biopsy channel 36 is related to time by the encoder, the spacing or distance between the tip center points of the ellipses can be controlled by the computer regardless of the speed with which the user pushes the sensor rod 10 into the channel. The computer calculates insertion distance from the encoder and repeats the tip center point and ellipse calculation for equal sequential insertion distances as the sensor rod 10 is pushed in the biopsy channel 36.

To take account of the twisting of the sensor rod 10 between the world coordinate system and the moving coordinate system, the twist angles of the sensor rod 10 can be measured from the outputs of the torsion strain gages 32 spaced along the length of the rod. These outputs can be inserted in the transformational matrix between the coordinate systems to calculate the rotational twist of the moving coordinate system relative to the world coordinate system.

Figure 7:
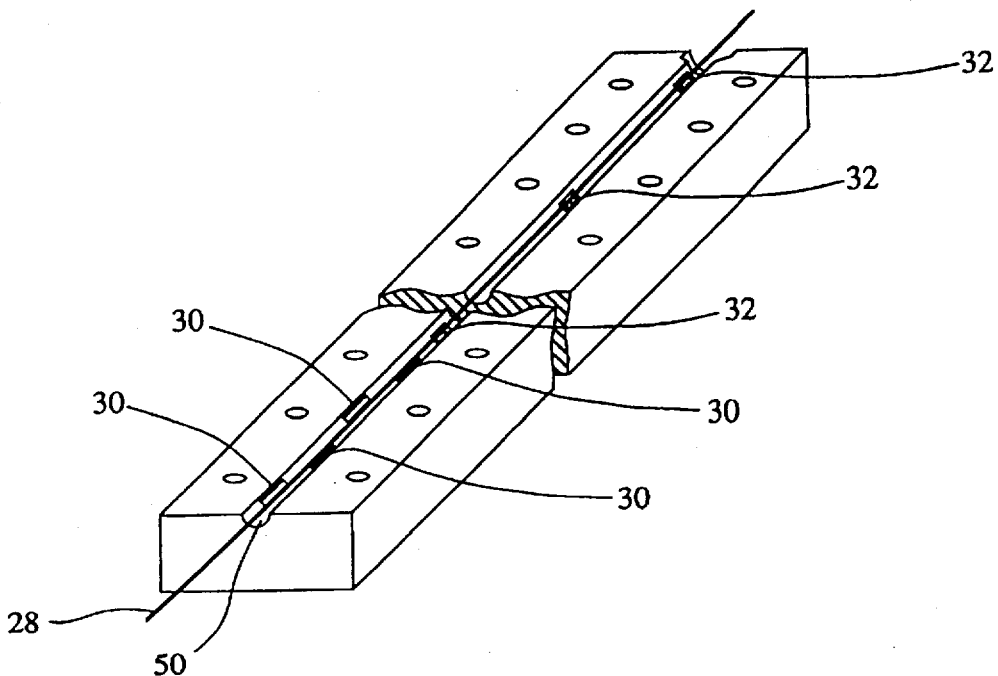
FIG. 7 illustrates a mold half for the manufacture of the sensor rod.

The preferred method of constructing the rod comprises a split cylindrical cavity 50 the length of the sensor rod 10 as shown in FIG. 7 wherein one of the mold halves is shown. The stainless steel wire 28 is brought taught along the axis of the cavity 50. The strain gages 30 and 32 are positioned in the mold halves and a suitable primer applied to the strain gages and wire 28. The primer may be applied to the strain gages 30 and 32 and the wire 28 before placement in the mold 50. The primer is selected for compatibility with the particular rubber formulation poured into the cavity 50 after the halves are brought together. Silicone rubber and urethane rubber have both been found suitable for the sensor rod 10. The primer is necessary to provide the adhesion necessary for the strain gages 30 and 32.

After the cured sensor rod 10 is removed from the cavity 50, the polytetrafluoroethylene sleeve 34 is shrunk fit over the sensor rod 10, thus encasing the entire assembly in a protective and relatively slippery surface for ease of insertion in the biopsy channel 36.

Although the sensor rod 10 has been described above as having torsional strain gages 32 spaced along substantially the full length of the rod with bending strain gages 30 over a relatively short bending head 24 other constructions can be envisioned. For example, referring back to FIG. 2 the head 24 may be formed as a separate part with the bending strain gages 30 there attached. The head 24 can then be attached adhesively or mechanically to a relatively less expensive flexible rod lacking the torsional strain gages 32 and wire 28. This construction can be used for imaging calculations that entirely do not require torsional data from the portion of the rod 10 behind the head 24.

By forming the head 24 as a separate part, a much shorter mold cavity 50 and wire 28 can be used, thus saving considerable tool and material expense for the sensor rod 10.

I claim:

1. In combination with an endoscope having a biopsy channel therethrough,
    a sensor comprising a flexible rod, a plurality of strain gages securely attached to the rod, at least some of the strain gages mounted parallel to the axis of the rod to provide a change in electrical impedance in response to bending of the rod, inelastic means in the rod to substantially prevent elongation of the rod during bending and means to measure the insertion distance of the sensor in the biopsy channel.

2. The endoscope and sensor of claim 1 wherein the rod is covered with a material easily slideable in the biopsy channel.

3. The endoscope and sensor of claim 1 wherein the strain gages are mounted on the surface of the rod at a plurality of axial locations, wherein the strain gages mounted parallel to the axis are located near one end of the rod and the other strain gages are generally spaced along the length of the flexible rod.

4. The endoscope and sensor of claim 3 wherein the surface of the rod and strain gages are covered with a material easily slideable in the biopsy channel.

5. The endoscope and sensor of claim 4 wherein the material covering the rod and strain gages is shrunk fit thereover.

6. The endoscope and sensor of claim 4 wherein the material covering the rod and strain gages is polytetrafluoroethylene.

7. The endoscope and sensor of claim 1 further comprising a second flexible rod lacking strain gages and affixed to one end of said flexible rod.

8. A sensor for an endoscope having a biopsy channel, the sensor comprising a bendable rod, a plurality of strain gages securely attached to the rod, at least some of the strain gages mounted to measure strain parallel to the axis of the rod to provide a change in electrical impedance in response to bending of the rod,
    separate inelastic means extending longitudinally through the rod to substantially prevent elongation of the rod during bending,
    and means to measure insertion distance of the sensor in a biopsy channel, wherein at least some of the strain gages are mounted to measure torsional strain of the rod to thereby provide a change in electrical output in response to twisting of the rod.

9. The sensor of claim 8 wherein the strain gages are mounted on the surface of the rod at a plurality of axial locations wherein the strain gages mounted to measure strain parallel to the rod axis are located near one end of the rod and the strain gages mounted to measure torsional strain of the rod are generally spaced along the length of the rod.

10. The sensor of claim 9 wherein the rod and strain gages are covered with a material easily slideable in an endoscope biopsy channel.

11. The sensor of claim 8 wherein the strain gages mounted to measure strain parallel to the axis of the rod are located near one end of the rod.

12. The sensor of claim 11 wherein the rod and strain gages are covered with a material easily slideable in an endoscope biopsy channel.

13. The sensor of claim 8 further comprising a second bendable rod lacking strain gages and affixed to one end of said bendable rod.

* * * * *